United States Patent
Oosterbroek et al.

(10) Patent No.: US 11,262,370 B2
(45) Date of Patent: Mar. 1, 2022

(54) METHOD FOR OPERATING A LABORATORY SYSTEM

(71) Applicant: Roche Diagnostics Operations, Inc., Indianapolis, IN (US)

(72) Inventors: Edwin Oosterbroek, Cham (CH); Urs Suter, Zurich (CH); Vaclav Cechticky, Baar (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 291 days.

(21) Appl. No.: 16/105,059

(22) Filed: Aug. 20, 2018

(65) Prior Publication Data

US 2019/0072575 A1    Mar. 7, 2019

(30) Foreign Application Priority Data

Sep. 1, 2017  (EP) .................................. 17189007

(51) Int. Cl.
*G01N 35/00*  (2006.01)
*G06Q 10/06*  (2012.01)

(52) U.S. Cl.
CPC ... *G01N 35/00871* (2013.01); *G01N 35/0092* (2013.01); *G06Q 10/0631* (2013.01)

(58) Field of Classification Search
CPC .............................................. G01N 35/00871
See application file for complete search history.

(56) References Cited

U.S. PATENT DOCUMENTS

| | | | |
|---|---|---|---|
| 2002/0147515 A1 | 10/2002 | Fava et al. | |
| 2005/0038676 A1* | 2/2005 | Showalter | G06Q 50/22 705/2 |
| 2014/0129172 A1 | 5/2014 | Eberhardt et al. | |
| 2015/0309058 A1 | 10/2015 | Kain et al. | |

FOREIGN PATENT DOCUMENTS

| | | |
|---|---|---|
| EP | 3182133 A1 | 6/2017 |
| WO | 2001/009618 A1 | 2/2001 |

* cited by examiner

*Primary Examiner* — Matthew D Krcha
(74) *Attorney, Agent, or Firm* — Roche Diagnostics Operations, Inc.

(57) ABSTRACT

A method for operating a laboratory system comprising laboratory instruments and a laboratory information system is presented. The method comprises grouping laboratory instruments into instrument cluster(s) and providing a cluster manager thereto. The plurality of laboratory instruments publishes their instrument resource descriptions. Each cluster manager maintains an inventory of cluster resources and publishes a list of processing capabilities of the instrument cluster. The laboratory information system assigns processing of test order(s) to instrument clusters. Each cluster manager assigns resources of the laboratory instruments corresponding to test orders from the laboratory information system in view of the inventory of cluster resources. Each laboratory instrument carries out the processing step(s) on the biological sample as instructed by the cluster manager.

11 Claims, 13 Drawing Sheets

METHOD FOR OPERATING A LABORATORY SYSTEM

CROSS-REFERENCE TO RELATED APPLICATIONS

This application is based on and claims priority to EP 17189007.2 filed Sep. 1, 2017, which is hereby incorporated by reference.

BACKGROUND

The present disclosure generally relates to a computer implemented method for operating a laboratory system for processing biological samples and to a laboratory system for processing biological samples.

In vitro diagnostic testing has a major effect on clinical decisions, providing physicians with pivotal information.

In analytical laboratories such as, clinical laboratories, a multitude of analyses on samples are executed by an analytical system in order to determine the physiological state of a patient. The kind of analytical test to be executed on a biological sample is typically specified as a test order which is typically registered and managed in a laboratory information system. According to established laboratory procedures, the laboratory information system maintains an inventory of the resources of all instruments of the laboratory system and in some cases maintains a current status of these resources. It then assigns resources of the laboratory instruments according to the test order. Known laboratory information systems then instruct the corresponding laboratory instrument(s) to carry out the respective processing step(s) on the biological sample based on each instrument's processing capabilities and current status.

This is however disadvantageous as such known laboratory systems are centrally managed by the laboratory information system. In laboratory systems of increased size with a high number of instruments, the central laboratory information system becomes very complex and may even be overloaded. The high complexity/load of the laboratory information system represents a single point of failure of the laboratory system—since the failure of the laboratory information system will inevitably lead to a halt in processing of any further test orders.

Furthermore, setting up the laboratory information system for a laboratory system comprising a high number of instruments is a very complex and therefore error-prone task, since a single laboratory information system needs to handle the resources/availability and capacity of all instruments to be able to distribute the processing steps of all test orders to the corresponding instruments.

In order to address the above-mentioned disadvantages of a single point of failure due to the high complexity and load of a central laboratory information system, attempts have been made to group instruments into groups, each group being managed by a dedicated instrument group manager. Currently instrument grouping is commonly implemented as a physical grouping, sometimes even including a dedicated sample transportation system. Also, each group of instruments has its own configuration system, isolated from higher level system configurations. This often leads to situations where for example a change of a reagent(s) used by one or more instruments of the group needs to be reconfigured manually not only at instrument/group level but also separately at the level of the entire laboratory system.

While such known laboratory systems with instrument grouping do address to some degree the high complexity of a centrally managed laboratory system, they suffer from a lack of flexibility as each group has to be set up and configured manually, wherein the extension of such a group by addition of an instrument or reconfiguration of a group needs to be accompanied by a manual reconfiguration of the corresponding instrument group manager. Furthermore, while such known laboratory systems with instrument grouping provide local management of the grouped instruments, the laboratory information system needs to manage a list of resources of each group of instruments to be able to instruct the correct group for each test order to carry out the respective processing step(s) on the biological sample based on each instrument's processing capabilities and current status.

Furthermore, laboratory systems have to deal with two types of laboratory instruments as far as their capability to fully or partially process a test order. While there are laboratory instruments which can carry out the entire processing of a test order, a second type of laboratory instruments comprise only resources to carry out a certain part of a test order. Centrally managing the completion of test orders by the latter type of instruments is particularly challenging in laboratories with a high number of instruments.

Currently known laboratory systems employ a single data-communication topology—usually a centralized topology. However, although for certain applications a centralized topology may be useful, for other applications, where e.g. large volumes of data need to be exchanged between a subset of instruments, a centralized communication topology is at risk of getting overloaded.

Therefore, there is a need for a laboratory system and method for operating a laboratory system that is both flexible and scalable in order to handle a high number of laboratory instruments and eliminate the need for manual (re)configuration upon changes in the processing capabilities and/or availability and/or capacity of any of these laboratory instruments as well as a need for a fault tolerant system to provide high availability of the overall laboratory system and a need for a solution that provides flexible data-communication topology.

SUMMARY

According to the present disclosure, a computer implemented method for operating a laboratory system comprising a plurality of laboratory instruments for processing biological samples and a laboratory information system is presented. The method can comprise grouping one or more of the plurality of laboratory instruments into one or more instrument cluster(s) and providing a cluster manager for each instrument cluster(s) and, within each instrument cluster, publishing the respective instrument resource description of each laboratory instrument(s) for the cluster manager. The instrument resource description can comprise a list of hardware and/or software resources of the laboratory instrument. The method can also comprise maintaining an inventory of cluster resources of the instrument cluster by each cluster manager. The inventory of cluster resources can comprise a consolidated collection based on the instrument resource descriptions of each of the laboratory instruments of the respective instrument cluster. The method can also comprise publishing a list of processing capabilities of the respective instrument cluster to the laboratory information system by each cluster manager. The list of processing capabilities can be indicative of processing steps that the respective instrument cluster is able to carry out based on the inventory of cluster resources. The method can also comprise receiving a biological sample by the laboratory system and receiving a test order corresponding to the biological sample by the laboratory information system. The test order can be indicative of processing step(s) to be carried out on respective biological sample. The method can also comprise assigning processing of the test order on the biological sample to the one or more instrument clusters by the laboratory information system according to the list of processing capabilities of the instrument clusters, forwarding one or more test order(s) by the laboratory information system to one or more cluster manager(s), receiving the test order(s) from the laboratory information system by the one or more cluster manager(s), assigning by each cluster manager resources of the plurality of laboratory instruments of the instrument cluster for the processing step(s) on the biological sample corresponding to the test order in view of the inventory of cluster resources, instructing one or more laboratory instrument(s) of the instrument cluster by each cluster manager to carry out the respective processing step(s) on the biological sample, and carrying out the respective processing step(s) on the biological sample by each laboratory instrument as instructed by the cluster manager.

Accordingly, it is a feature of the embodiments of the present disclosure to provide for a laboratory system and method for operating a laboratory system that is both flexible and scalable in order to handle a high number of laboratory instruments and eliminate the need for manual (re)configuration upon changes in the processing capabilities and/or availability and/or capacity of any of these laboratory instruments, that has a fault tolerant system to provide high availability of the overall laboratory system and to provide flexible data-communication topology. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
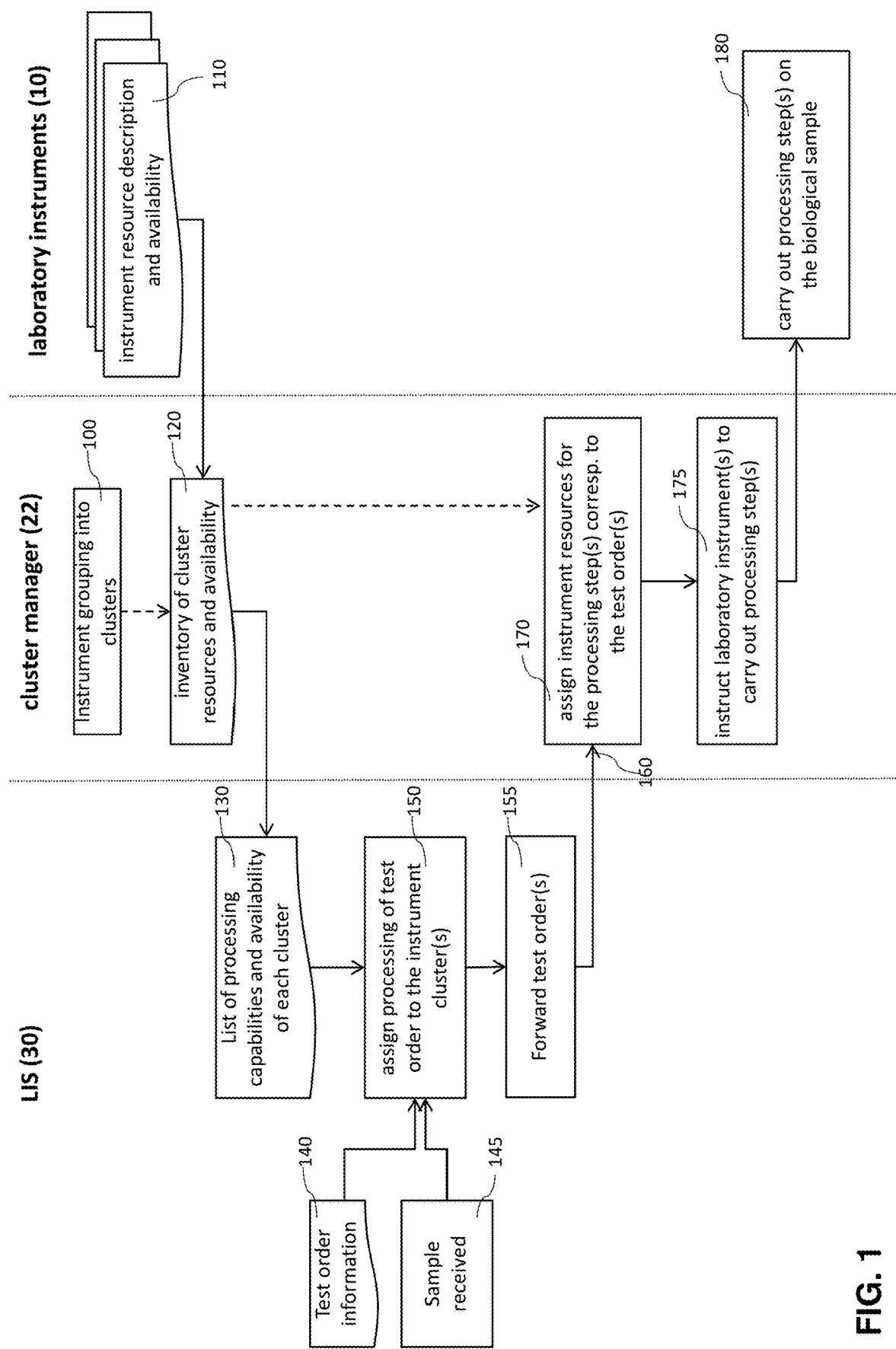
FIG. 1 illustrates a swim-lane diagram illustrating plug and play-like configuration of instrument cluster(s) and abstraction of instrument resource handling from the perspective of the laboratory information system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Disclosed herein is a computer implemented method for operating a laboratory system comprising a plurality of laboratory instruments for processing biological samples and a laboratory information system. Embodiments of the disclosed method can comprise the steps:

grouping one or more of the plurality of laboratory instruments into one or more instrument cluster(s) and providing a cluster manager for each instrument cluster(s);

within each instrument cluster, each laboratory instrument(s) publishing their respective instrument resource description for the cluster manager, the instrument resource description comprising a list of hardware and/or software resources of the laboratory instrument;

each cluster manager maintaining an inventory of cluster resources of the instrument cluster, the inventory of cluster resources comprising a consolidated collection based on the instrument resource descriptions of each of the laboratory instruments of the respective instrument cluster;

each cluster manager publishing a list of processing capabilities of the respective instrument cluster to the laboratory information system (and/or a "higher level" cluster manager), the list of processing capabilities being indicative of processing steps that the respective instrument cluster is able to carry out based on the inventory of cluster resources;

the laboratory system receiving a biological sample;

the laboratory information system receiving a test order corresponding to the biological sample, the test order being indicative of processing step(s) to be carried out on respective biological sample;

the laboratory information system assigning processing of the test order on the biological sample to the one or more instrument clusters according to the list of processing capabilities of the instrument clusters;

the laboratory information system forwarding one or more test order(s) to one or more cluster manager(s);

the one or more cluster manager(s) receiving the test order from the laboratory information system;

each cluster manager assigning resources of the plurality of laboratory instruments of the instrument cluster for the processing step(s) on the respective biological sample corresponding to the test order in view of the inventory of cluster resources;

each cluster manager instructing one or more laboratory instrument(s) of the instrument cluster to carry out the respective processing step(s) on the biological sample; and each laboratory instrument carrying out the respective processing step(s) on the biological sample as instructed by the cluster manager.

According to further embodiments, disclosed herein, the method further can comprise the steps:

one or more laboratory instrument(s) transmitting an analytical result to the cluster manager, the analytical result comprising a measurement value and/or an output of a data analysis; and one or more cluster manager(s) forwarding the analytical result to the laboratory information system.

Further disclosed herein is a laboratory system comprising a plurality of laboratory instruments for processing biological samples; a laboratory information system and one or more instrument clusters, each instrument cluster comprising a cluster manager, wherein the laboratory system can be configured to carry out the embodiments of the method disclosed.

Further disclosed herein is a computer-readable medium storing instructions thereon which when executed by a computer system can control the computer system to perform the embodiments of the method disclosed.

Embodiments of the disclosed method/system can be particularly advantageous as they can provide scalability by way of organizing laboratory instruments into instrument clusters and reduce complexity by way of managing each instrument cluster by a dedicated cluster manager. Furthermore, embodiments disclosed herein can eliminate the single point of failure of known laboratory systems by way of distributing the allocation of laboratory resources to the clusters. Additionally, or alternatively, embodiments disclosed herein can eliminate the single point of failure by providing the appropriate data-communication topology for the particular application. Also, a high degree of flexibility/(re)configurability can be ensured by way of a plug-and-play approach in that the laboratory instruments can publish their respective instrument resource description to the respective cluster managers which can then maintain an inventory of cluster resources of the respective instrument cluster and allocate resources within the cluster accordingly. In other words, a configuration or a status of an instrument can be migrated automatically to a higher level cluster or laboratory system level, without the need for manual configuration. Thus a dynamic (re)configuration of instrument cluster(s) or even the entire laboratory system can be enabled without the need for manual intervention, including (re)configuration to deal with sudden and/or planned unavailability of an instrument or part thereof.

In addition, embodiments disclosed herein can be advantageous due to the abstraction that can be provided by the cluster manager publishing a list of processing capabilities of the cluster based on the inventory of cluster resources. In this way, the management of the instrument resources of each cluster can be transparent to the laboratory information system of the laboratory which can be presented with up-to-date lists of processing capabilities of each cluster. Thus, the laboratory information system may no be longer overloaded by the tasks of managing all instrument resources and can plan processing of test orders based only on the processing capabilities of instrument clusters, delegating the resource (instruments, consumables, etc.) management to the cluster managers. This level of abstraction can offer a significant advantage over known laboratory systems with centralized resource management. Furthermore, the abstraction can also enable easier (re)configuration of instruments and instrument clusters, where a (re)configuration can be migrated as a "resource pool" to a higher level cluster or laboratory system level, even dynamically/at run-time.

The term 'laboratory instrument' as used herein can encompass any apparatus or apparatus component operable to execute one or more processing steps/workflow steps on one or more biological samples. The expression 'processing steps' thereby can refer to physically executed processing steps such as centrifugation, pipetting, aliquotation, reagent preparation, quality control QC preparation, sequencing library preparation, incubation, sample analysis and also sample transportation. The term 'laboratory instrument' can cover pre-analytical instruments, post-analytical and analytical instruments as well as transportation system, or modules thereof. Furthermore, the term laboratory instrument can comprise data processing apparatus configured to process analytical data.

The expression 'laboratory instrument' as used herein can encompass any monolithic or multi-modular laboratory device comprising one or more lab-devices or operative units which can be operable to execute an analytical test on one or more biological samples.

The term 'pre-analytical instrument' as used herein can comprise one or more lab-devices for executing one or more pre-analytical processing steps on one or more biological samples, thereby preparing the samples for one or more succeeding analytical tests. A pre-analytical processing step can be, for example, a centrifugation step, a capping-, decapping- or recapping step, a sealing, de-sealing step, an aliquotation step, dilution of a sample and the like.

The term 'post-analytical instrument' as used herein can encompass any laboratory instrument being operable to automatically process and/or store one or more biological samples. Post-analytical processing steps may comprise a recapping step, a step for unloading a sample from an analytical system or a step for storing said sample to in a storage unit or to a unit for collecting biological waste.

The term 'analyzer'/'analytical instrument' as used herein can encompass any apparatus or apparatus component configured to obtain a measurement value. An analyzer can be operable to determine via various chemical, biological, physical, optical, electro-chemical or other technical procedures a parameter value of the sample or a component thereof. An analyzer may be operable to measure the parameter of the sample or of at least one analyte and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzer are clinical chemistry analyzers, coagulation chemistry analyzers, immunochemistry analyzers, urine analyzers, nucleic acid analyzers, tissue analyzers (including morphological stainers and histochemical stainers) used to detect the result of chemical or biological reactions or to monitor the progress of chemical or biological reactions.

The term 'transportation system' as used herein can encompass any system configured to convey required materials and/or samples between different laboratory instrument(s) within a laboratory system. In particular embodiments, the transport system can also be used to store at least intermediately, the required materials on the transport system. Materials may be biological samples or any required consumable to perform a laboratory process. Various transportation systems may be used to transport samples between stations of a laboratory analysis system, such as one dimensional belt-driven sample transportation systems or multi-dimensional transportation systems. The materials may be provided in material containers which can be placed in transport carriers on the transport system. The transport carriers may receive one single or multiple material containers. The term 'laboratory system' as used herein can encompass any system for the use in a laboratory comprising a plurality of laboratory instruments operatively connected to a control unit.

The term 'laboratory information system' as used herein can encompass any physical or virtual processing device configured to receive and manage test orders corresponding to biological samples, the test orders being indicative of processing step(s) to be carried out on respective biological sample. Managing of the test orders can comprise, in particular, the forwarding of the test order to one or more laboratory instruments respectively instrument clusters. In some embodiments, the laboratory information system can be integral with a data management unit, can be comprised by an on premise or cloud based server computer and/or be part of one instrument or even distributed across multiple instruments of the laboratory system.

The term 'communication network' as used herein can encompass any type of wireless network, such as a WIFI, GSM, UMTS or other wireless digital network or a cable based network, such as Ethernet or the like. For example, the communication network can comprise a combination of wired and wireless networks. In embodiments wherein units of the system are comprised within one laboratory instrument, the communication network can comprise communication channels within an instrument.

The term 'instrument cluster' as used herein can refer to a group of mutually connected (logically and/or physically connected) laboratory instruments to achieve benefits over single stand-alone instruments, like obtaining seamless workflow integration or grouping of instruments with identical or similar capabilities. An instrument cluster can typically be positioned between a laboratory information system and single instruments. Laboratory instruments belonging to the same cluster may, but do not need to be located in each other's vicinity (logical and/or physical clustering). If spatially clustered, the modules of a cluster can be physically separated entities, each with their own housing, or modules included into one or multiple housings.

A cluster may comprise instruments or sub-systems of instruments. Also according to embodiments disclosed herein, a laboratory instrument may comprise more than one instrument cluster. In such embodiments, the instrument can be referred to as being shared between multiple clusters. For example, a pre- or post-analytic instrument may be shared between several clusters of different types of laboratory instruments which share a common need for pre- and post-analytical instruments, such as a centrifuge respectively a sample archive unit being shared regardless of the type of analytical instruments of various clusters. Furthermore, an instrument cluster may comprise one or more instrument clusters, such that a hierarchy of clusters is formed.

The term 'user interface' as used herein can encompass any suitable piece of software and/or hardware for interactions between an operator and a machine, including but not limited to a graphical user interface for receiving as input a command from an operator and also to provide feedback and convey information thereto. Also, a system/device may expose several user interfaces to serve different kinds of users/operators.

The term 'workflow' as used herein can refer to a collection of workflow steps/processing steps. According to some embodiments, the workflow can define a sequence in which the processing steps can be carried out.

The term 'workflow step' or 'processing step' as used herein can encompass any activity belonging to a workflow. The activity can be of an elementary or complex nature and can typically be performed at or by one or more instrument(s) as a processing step.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium.

In some embodiments, the sample can be suspected to contain a certain antigen or nucleic acid.

A 'STAT sample' can be a sample which needs to be processed and analyzed very urgently as the analysis result may be of life-crucial importance for a patient.

The terms 'aliquot', 'patient sample aliquot' and 'biological sample aliquot' can refer to a portion of the sample, patient sample or biological sample usually obtained by aliquoting, i.e. dividing the biological sample, such as, for example using a pipetting process. In this context, the biological sample can be referred to as primary sample and the tube in which it resides can be referred to as primary sample tube while the sample portions divided from the primary sample can be called aliquots and the tube(s) in which they reside can be referred to as aliquot tubes or secondary tubes. An aliquot(s) of a biological sample can usually be created into a secondary sample tube or sample plate well separate from the primary sample tube or sample plate well.

The term 'analysis' or 'analytical test' as used herein can encompass a laboratory procedure characterizing a parameter of a biological sample, e.g. light absorption, fluorescence, electrical potential or other physical or chemical characteristics of the reaction to provide the measurement data.

The term 'test order' as used herein can refer to any data object, computer loadable data structure, modulated data representing such data indicative of one or more laboratory processing steps to be executed on a particular biological sample. For example, a test order record may be a file or an entry in a database. According to embodiments disclosed herein, a test order can indicate a test order for an analytical test if, for example, the test order comprises or is stored in association with an identifier of an analytical test to be executed on a particular sample. Alternatively, or additionally, the test order may refer to purely pre- and/or post-analytical processing steps to be performed on the biological sample. Furthermore, the test order may be indicative of data processing steps to be performed on analytical data related to a biological sample, in particular data processing steps on analytical data obtained by measurement of the biological sample.

The term 'analytical data' as used herein can encompass any data that can be descriptive of a result or partial result of a measurement or processing of a biological sample. In the case of a calibration, the analytical data can comprise the calibration result, i.e. calibration data. In particular, the analytical data can comprise an identifier of the sample for which the analysis has been performed and data being descriptive of a result of the analysis, such as measurement data.

Referring initially to FIG. 1, FIG. 1 shows a swim-lane diagram depicting an embodiment of the disclosed method, illustrating plug and play-like configuration of instrument cluster(s) 20 and abstraction of instrument resource handling from the perspective of the laboratory information system 30.

As shown in FIG. 1, in a first step 100, one or more of the plurality of laboratory instruments 10, 10PRE, 10POST, 10AI, 10VI, 10TRANS can be grouped into one or more instrument cluster(s) 20. This grouping/clustering of step 100 can be, according to various embodiments, a physical and/or logical clustering of instruments, wherein instruments of a cluster may or may not be in proximity to each other. Step 100 of grouping/clustering can comprise the provision of a cluster manager 22 for each instrument cluster(s) 20.

According to various embodiments, the cluster manager 22 of one or more of the instrument clusters 20 can comprise one or more of the plurality of laboratory instruments 10, 10PRE, 10POST, 10AI, 10VI, 10TRANS. This cluster manager 22 comprised by a laboratory instrument 10, 10PRE, 10POST, 10AI, 10VI, 10TRANS can be configured such as to wake up from a standby mode when an additional laboratory instrument is added to the same instrument cluster 20 and can be further configured to switch into the standby mode when the laboratory instrument 10, 10PRE, 10POST, 10AI, 10VI, 10TRANS is the only instrument in the respective instrument cluster 20. Such embodiments where a cluster manager 22 is integrated into an instrument can be advantageous as a system functionality can be obtained (e.g., to share resources between instruments and/or to integrate results communication or remote service via one central cluster node) without the need for additional hardware. This can be especially advantageous for low-cost small instruments, such as Point of Care instruments. The cluster manager 22 can be activated (wake-up) via manual control or an automated selection procedure e.g., some type of instruments can be selected first before others get selected. Identical instruments 10, 10PRE, 10POST, 10AI, 10VI, 10TRANS, each with an integrated cluster manager 22 can, for example, select the cluster manager to be activated via a random process.

According to further embodiments, at least one instrument cluster 20 can comprise two or more cluster managers 22. In such embodiments, the two or more cluster managers 22 can be configured such that, at any time, only one of the two or more cluster managers 22 can be active and can be further configured such that, if a first of the two or more cluster managers 22 becomes inoperable, a second of the two or more cluster managers 22 can be activated.

In a further step 110, within each instrument cluster 20, each laboratory instrument(s) 10, 10PRE, 10POST, 10AI, 10VI, 10TRANS can publish their respective instrument resource description for the cluster manager 22. The instrument resource description can comprise a list of hardware and/or software resources of the laboratory instrument for processing biological samples and/or analytical data. For example, an instrument resource can comprise an analytical module operable to determine via various chemical, biological, physical, optical or other technical procedures a parameter value of the sample or a component thereof. Correspondingly, the instrument resource description can list the assays the analytical instrument resource is capable of performing and/or list the analytes it can detect/quantify in a biological sample.

An instrument resource may also comprise pre-analytical instrument resources like a sample handling module such as a pipettor, an aliquoter or capper/decapper, a centrifuge, etc. Correspondingly, the instrument resource description can list for example what samples can a centrifuge handle and up to what centrifugal acceleration.

Furthermore, an instrument resource may comprise post-analytical instrument resources operable to automatically process and/or store one or more biological samples. Post-analytical resources may comprise a recapper, a sample unloader for unloading samples from an analytical system or a transport system for transporting the sample, or a storage unit or a unit for collecting biological waste. Correspondingly, the instrument resource description can, for example, describe the type of samples (including also type of test performed on the sample) a post-analytical instrument can receive and recap, respectively store in a refrigerator, and at what temperature.

According to further embodiments, the instrument resource descriptions of the laboratory instruments 10, 10PRE, 10POST, 10AI, 10VI, 10TRANS can further comprise an indication of current and/or estimated availability of the hardware and/or software resources. As used herein, availability can be an indication whether a certain resource of an instrument 10, 10PRE, 10POST, 10AI, 10VI, 10TRANS or capability of instrument cluster 20 is operational or is expected to be operational at a certain time. In other words, availability can refer to the current and/or estimated status of the respective resource such as for example "online"/"offline" or "operational"/"non-operational." A resource can be unavailable, for example, due to an error of the resource but also due to an expiration of the latest quality control—in the case of an analytical resource. A further reason why a resource may not be available can be the absence of required consumables such as a regent, a disposable pipette, sample plate, and the like. In the case such consumables required by an instrument resource are running low, there can be cases where the current availability can still be "true" while the estimated availability can be "false." Accordingly, the cluster manager 22 may not assign more test orders to this resource.

According to further embodiments, the instrument resource descriptions of the laboratory instruments 10, 10PRE, 10POST, 10AI, 10VI, 10TRANS can further comprise an indication of current and/or estimated capacity of the hardware and/or software resources. As its name implies, the capacity of a resource can refer to a level of availability. For example, the current and/or estimated capacity of an analytical instrument resource can indicate the number of analytical tests the respective analytical laboratory instrument 10AI can process per hour.

For example, in the case of a post-analytical instrument 10POST, the capacity of its sample storage resource can indicate how many samples the instrument 10POST can store (in view of its current occupancy).

Based on the instrument resource descriptions of each of the laboratory instruments 10, 10PRE, 10POST, 10AI, 10VI, 10TRANS received, in a step 120, each cluster manager 22 can establish and maintain an inventory of cluster resources. The inventory of cluster resources can comprise a consolidated collection based on the instrument resource descriptions of each of the laboratory instruments 10, 10PRE, 10POST, 10AI, 10VI, 10TRANS of the respective instrument cluster 20.

In a further step 130, each cluster manager 22 can publish a list of processing capabilities of the respective instrument cluster 20 to the laboratory information system 30. The list of processing capabilities can be indicative of processing steps that the respective instrument cluster 20 is able to carry out based on the inventory of cluster resources. In other words, the list of processing capabilities can comprise processing steps that any of the laboratory instruments 10, 10PRE, 10POST, 10AI, 10VI, 10TRANS of the respective can carry out. It can be noted that when several instruments 10, 10PRE, 10POST, 10A in a cluster 20 can perform the same processing step, this can be consolidated as one processing capability of the cluster, however with a higher capacity/availability. As part of step 130, the laboratory information system 30 can receive the list of processing capabilities of the instrument clusters 20.

According to further embodiments, the list of processing capabilities of the respective instrument cluster 20 can further comprise an indication of current and/or estimated availability to carry the respective processing steps.

According to further embodiments, the list of processing capabilities of the respective instrument cluster 20 can further comprise an indication of current and/or estimated capacity to carry the respective processing steps.

In steps 140 and 145, which can occur in reverse order, the laboratory information system 30 can receive a test order corresponding to a biological sample, respectively, the sample can be received by the laboratory system 1 such as, for example, by a pre-analytical instrument 10PRE of the laboratory system 1, such as a sample loader. The test order can be indicative of the processing step(s) to be carried out on respective biological sample. According to various embodiments, the test order can list the specific processing steps to be carried out and/or indicate a workflow to be carried out, which, in turn, can be indicative of the particular processing steps. The laboratory information system 30 can be configured such as to translate the test orders into the particular processing steps to be carried out, in particular by way reference to a database/look-up table. For example, if a test order for a certain analytical test is received by the laboratory information system from a host system 40, the laboratory information system 30 can look up in a database what particular processing steps need to be carried out in order to perform that test order, e.g. sample preparation (such as centrifugation) followed by sample testing and finally sample archiving, and the like.

Once the laboratory information system 30 has received the test order and the sample has entered the laboratory, in a step 150, the laboratory information system 30 can assign the processing of the test order on the biological sample to the one or more instrument clusters 20 according to the list of processing capabilities of the instrument clusters 20. It can be emphasized that the particular details of which instrument(s) can process the sample and how the corresponding resources can be handled, etc., can be transparent to the laboratory information system 30, which only needs to be aware of is the list of processing capabilities of the instrument clusters 20 and assign the processing of the sample to one which has the required capability. In a step 155 following the assignment of the process of the test order to the one or more instrument cluster(s) 20, the laboratory information system 30 can forward one or more test order(s) to one or more cluster manager(s) 22.

According to embodiments, the step of transmitting the test orders to the cluster manager(s) 22 can be implemented as a publisher-subscriber (pub-sub) and/or request-reply and/or broadcast messaging pattern (non-exhaustive list).

According to the pub-sub messaging pattern, the cluster manager(s) 22 can subscribe to messages from the laboratory information system 30, while the laboratory information system 30 can publish messages (test orders) to one or more of the cluster manager(s) 22. In other words, the laboratory information system 22 can "tell" the respective cluster manager 22 what test order to process for particular biological sample.

According to the request-reply messaging pattern, the cluster manager 22 can send a request (a query) to the laboratory information system 30, "asking" what test order to carry out for a particular biological sample. In response to the query the laboratory information system 30 can transmit the test order as response to the cluster manager(s) 22. In other words, the cluster manager 22 can pull the test order from the laboratory information system 30, usually upon receipt/identification of a sample.

In a following step 160, the one or more cluster manager(s) 22 can receive the test order from the laboratory information system 30.

Once having received the test order(s), in a step 170, the cluster manager(s) 22 can assign resources of the plurality of laboratory instruments 10, 10PRE, 10POST, 10AI, 10VI, 10TRANS of the instrument cluster 20 for the processing step(s) on the respective biological sample corresponding to the test order(s) in view of the inventory of cluster resources. The expression "in view of the inventory of cluster resources" can refer to the process by which the cluster manager(s) 22 can verify the availability and/or capacity of all required resources of the instrument cluster 20 and correlate it with resources required for processing the biological sample according to the processing request instruction and can assign the processing to one or more laboratory instrument(s) 10, 10PRE, 10POST, 10AI, 10VI, 10TRANS accordingly.

According to some embodiments, the cluster manager 22 can allocate resources of the plurality of laboratory instruments 10, 10PRE, 10POST, 10AI, 10VI, 10TRANS for the processing step(s) on the respective biological sample in view of the availability and/or capacity of the resources of the laboratory instruments of the respective instrument cluster to provide load balancing between laboratory instruments 10, 10PRE, 10POST, 10AI, 10VI, 10TRANS with the same resources or similar resources. Load balancing of instruments can be advantageous in order to optimize the usage/aging of instruments with common resources.

According to further embodiments, the cluster manager 22 can allocate resources of the plurality of laboratory instruments 10, 10PRE, 10POST, 10AI, 10VI, 10TRANS for the processing step(s) on the respective biological sample in view of the availability and/or capacity of the resources of the laboratory instruments of the respective instrument cluster to ensure timely processing of the biological sample. For example, an instrument cluster 20 may comprise multiple laboratory instruments 10, 10PRE, 10POST, 10AI, 10VI, 10TRANS which can perform the same processing steps, but while one laboratory instrument 10, 10PRE, 10POST, 10AI, 10VI, 10TRANS can be optimized for high throughput, the other one can be configured to carry out a broader variety of less-frequently ordered processing steps. In this case, samples which are not so urgent can be assigned to the first, while urgent samples STAT can be assigned to the later laboratory instrument 10, 10PRE, 10POST, 10AI, 10VI, 10TRANS.

Following step 170 of assignment of the resources of the plurality of laboratory instruments 10, 10PRE, 10POST, 10AI, 10VI, 10TRANS for processing the biological sample, in a step 175, the one or more laboratory instrument(s) 10, 10PRE, 10POST, 10AI, 10VI, 10TRANS of the instrument cluster 20 can query the cluster manager 22 as to which processing steps to carry out on the biological sample. Correspondingly, in a step 180, the laboratory instrument(s) 10, 10PRE, 10POST, 10AI, 10VI, 10TRANS can carry out the respective processing step(s) on the biological sample as instructed by the cluster manager 22.

According to some embodiments, one or more of the plurality of laboratory instruments 10, 10PRE, 10POST, 10AI, 10VI, 10TRANS can publish an update of its instrument resource descriptions at regular intervals and/or upon a change of its hardware and/or software resources. Correspondingly, one or more of the cluster managers 22 can update the inventory of cluster resources based on the update(s) of instrument resource descriptions.

According to various embodiments, the update of instrument resource descriptions can be based on a push or pull approach, wherein either the laboratory instrument(s) 10, 10PRE, 10POST, 10AI, 10VI, 10TRANS can publish the update of instrument resource descriptions or the cluster manager 22 can query the instruments. For example, the cluster managers 22 can monitor a so-called heartbeat of the laboratory instruments 10, 10PRE, 10POST, 10AI, 10VI, 10TRANS, the absence thereof being indicative that the instrument is not available.

Figure 2A:
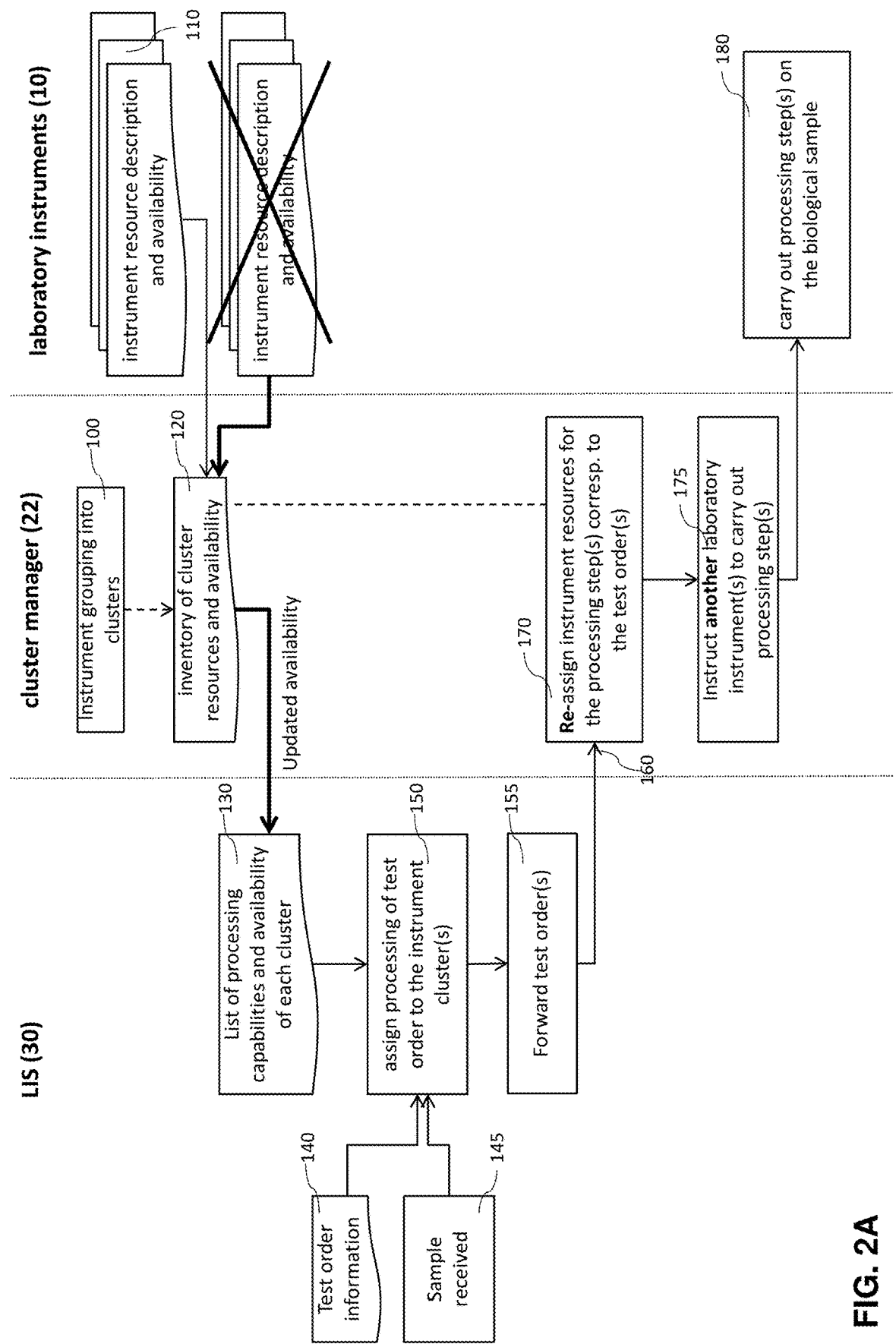
FIG. 2A illustrates a swim-lane diagram illustrating reconfiguration of an instrument cluster not affecting the processing capabilities of the cluster, only the availability thereof according to an embodiment of the present disclosure.

FIG. 2A shows a swim-lane diagram depicting a use case of reconfiguration of an instrument cluster not affecting the processing capabilities of the cluster—only the availability thereof. As illustrated on this figure, when one or more of the laboratory instrument(s) 10, 10PRE, 10POST, 10AI, 10VI, 10TRANS of an instrument cluster 20 become unavailable (illustrated by being crossed out), the cluster manager 22 can become aware of this change in instrument availability and can update the availability of its inventory of cluster resources. FIG. 2A illustrates a use-case when the unavailability of a laboratory instrument(s) 10, 10PRE, 10POST, 10AI, 10VI, 10TRANS can be compensated by other laboratory instrument(s) 10, 10PRE, 10POST, 10AI, 10VI, 10TRANS of the same cluster, which results in no change in the processing capabilities of the cluster, but only has an effect on availability/capacity thereof. In such case—as far as processing capabilities are concerned—the fallout of laboratory instrument(s) 10, 10PRE, 10POST, 10AI, 10VI, 10TRANS can be completely transparent to the laboratory information system 30. As such, the instrument cluster 20 can therefore be self-managing. In other words, if upon updating the inventory of cluster resources based on the update(s) of instrument resource descriptions, the overall availability and/or capacity of the instrument cluster 20 to carry out a particular processing step can be changed, the cluster manager 22 can transmit an updated list of processing capabilities to the laboratory information system 30 such as, for example, updating the availability and/or capacity to carry the particular processing step.

Figure 2B:
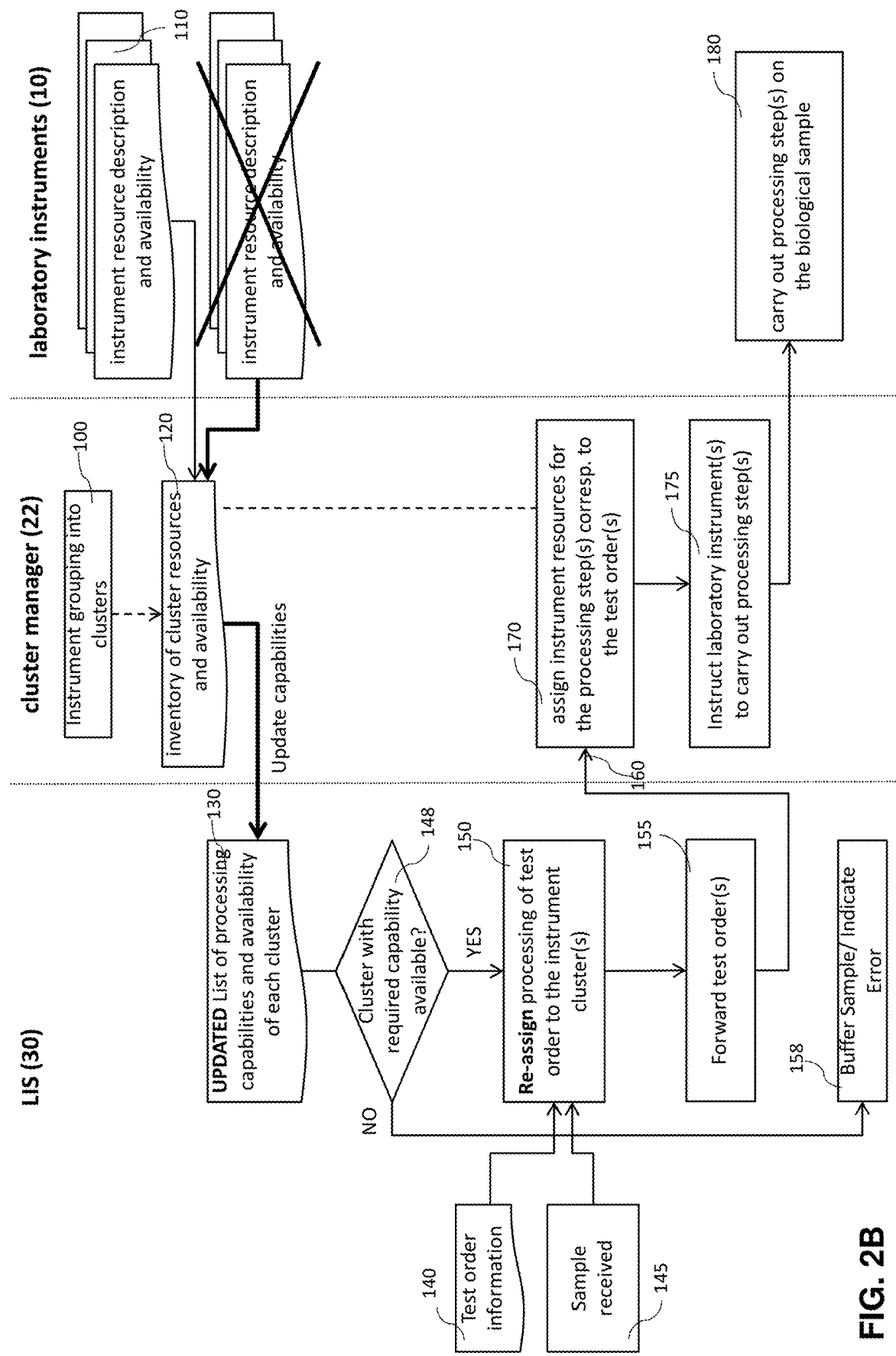
FIG. 2B illustrates a swim-lane diagram illustrating reconfiguration of an instrument cluster which affects the processing capabilities of the cluster according to an embodiment of the present disclosure.

On the other hand, FIG. 2B shows a swim-lane diagram depicting a use-case of reconfiguration of an instrument cluster 20 which does affect the processing capabilities of the instrument cluster 20. As illustrated on this figure, if the only laboratory instrument(s) 10, 10PRE, 10POST, 10AI, 10VI, 10TRANS having a particular instrument resource become(s) unavailable, not only the cluster's own inventory of resources but also the list of processing capabilities can be updated to reflect that the instrument cluster 20 now lacks a certain capability. Hence, if upon updating the inventory of cluster resources based on the update(s) of instrument resource descriptions, the respective instrument cluster 20 can no longer be able to carry out a particular processing step, the cluster manager 22 can transmit an updated list of processing capabilities to the laboratory information system 30.

In a step 148, based on the updated list of processing capabilities, the laboratory information system 30 can check whether any of the instrument clusters 20 have the capability required to process the biological sample according to the test order. If an instrument cluster 20 with such capabilities is available, the laboratory information system 30 can re-assign the processing of test orders on the biological sample(s) to this instrument cluster(s) (20). If none of the instrument clusters 20 have the required capability to process the biological sample according to the test order, in a step 158, the laboratory information system 30 can indicate an error. Alternatively, or additionally, the laboratory information system 30 can redirect the biological sample to a buffer and/or error location until such instrument cluster 20 with the required capability becomes available. Alternatively, or additionally if none of the instrument clusters 20 have the required availability to process the biological sample according to the test order, one of the instrument clusters 20 can accept the test order and store the biological sample in a buffer module until the required resource is available again or until a certain timeout expires/is about to expire.

Figure 3A:
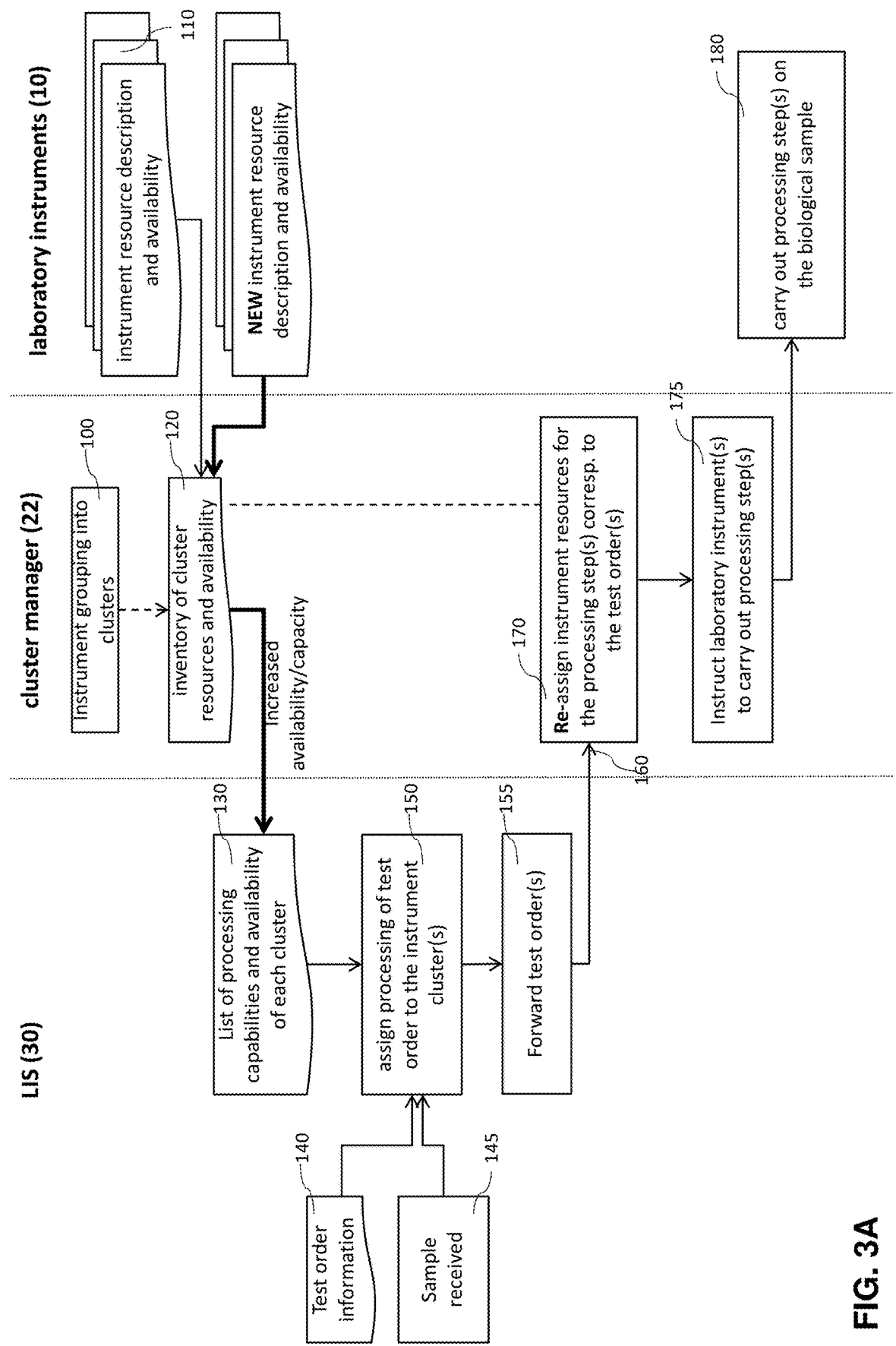
FIG. 3A illustrates a swim-lane diagram illustrating plug and play-like extension of an instrument cluster by addition of an instrument, extension not affecting the processing capabilities of the cluster but increasing availability and/or capacity thereof according to an embodiment of the present disclosure.

Turning to FIG. 3A, a swim-lane diagram is shown depicting an embodiment of the disclosed method, illustrating plug and play-like extension of an instrument cluster 20 by addition of a new laboratory instrument 10, 10PRE, 10POST, 10AI, 10VI, 10TRANS. The extension illustrated on FIG. 3A does not affect the processing capabilities of the cluster but does increase the availability and/or capacity thereof. In the use-case shown here, only the capacity and/or availability of the instrument cluster 20 can change but not the processing capabilities thereof. The capacity of a cluster 20 may be easily increased in a plug-and-play like fashion by simply adding an extra instrument 10, 10PRE, 10POST, 10AI, 10VI, 10TRANS. But not only capacity, but also availability can be increased in this way, since having an extra instrument 10, 10PRE, 10POST, 10AI, 10VI, 10TRANS with the same (or equivalent) resources can ensure greater availability in the case one of the instruments 10, 10PRE, 10POST, 10AI, 10VI, 10TRANS needs maintenance or is unavailable for any reason, such as lack of consumables.

Figure 3B:
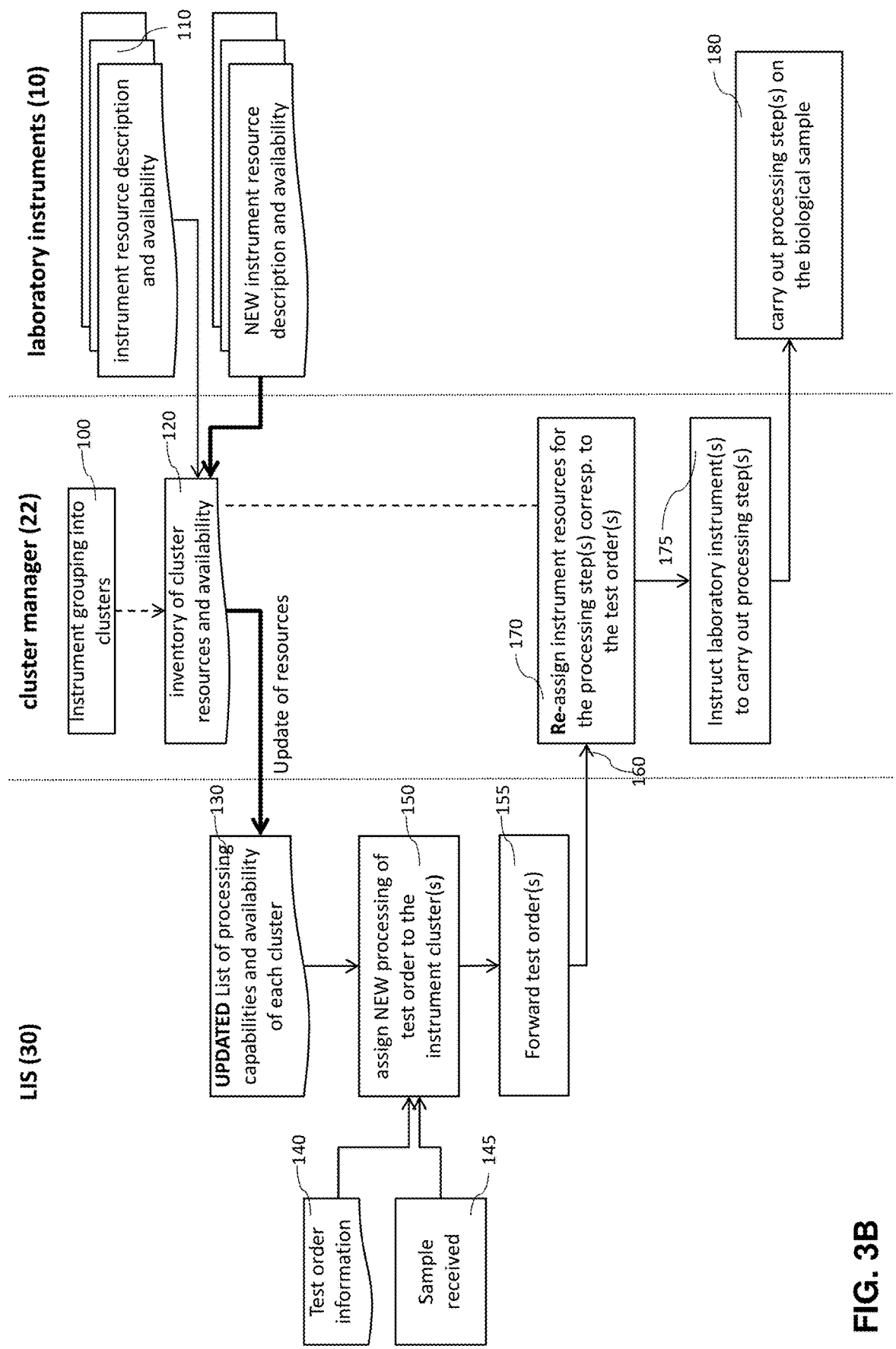
FIG. 3B illustrates a swim-lane diagram illustrating plug and play-like extension of an instrument cluster by addition of an instrument, extending the processing capabilities of the cluster according to an embodiment of the present disclosure.

FIG. 3B shows a swim-lane diagram depicting a use-case where an instrument cluster is extended by addition of a new laboratory instrument 10, 10PRE, 10POST, 10AI, 10VI, 10TRANS which extends the processing capabilities of the cluster. In this case not only the inventory of cluster resources but also the list of processing capabilities of the respective instrument cluster 20 can be updated and the update can be transmitted to the laboratory information system 30. Hence, following the extension of the cluster's 20 capabilities, the laboratory information system 30 can assign new test orders for processing biological samples to the extended instrument cluster 20, orders which either cannot be processed before the illustrated extension or would have been processed by a different instrument cluster 20.

Figure 4:
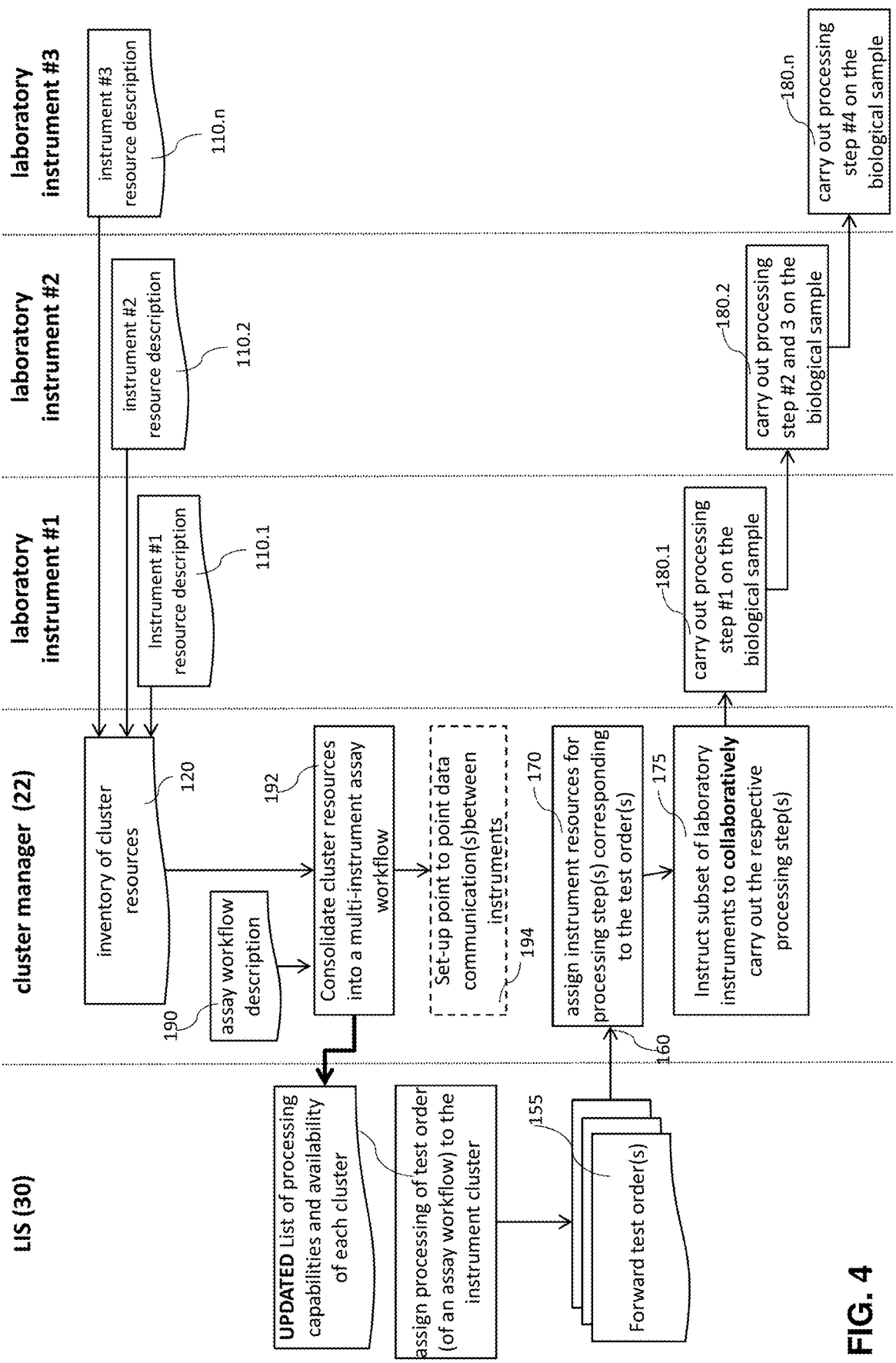
FIG. 4 illustrates a swim-lane diagram illustrating the configuration of a multi-instrument assay workflow within an instrument cluster according to an embodiment of the present disclosure.

Another feature of further embodiments is related to multi-instrument assay workflows, the setting up of which is illustrated on FIG. 4. Quite often there can be test orders for processing a biological sample which can require processing steps that cannot all be performed by one single instrument. Instead, the biological sample can be collaboratively processed by a plurality of laboratory instruments 10, 10PRE, 10POST, 10AI, 10VI, 10TRANS—either in sequence or simultaneously (in which case aliquots of the sample can be created). This process can hereafter be referred to as a multi-instrument assay workflow 12. For example, a biological sample can first be processed by a pre-analytical instrument 10PRE for sample preparation. Following sample preparation, the same sample can be processed by an analytical instrument 10AI for providing a measurement value indicative of the presence/concentration of an analyte in the biological sample. Finally, the biological sample can be processed by a post-analytical instrument 10POST, for example to be archived.

In order to configure a multi-instrument assay workflow 12, in a step 190, the cluster manager 22 can retrieve an assay workflow description (from a look-up table, a database or the like), the assay workflow description comprising a list and sequence of processing steps to be carried out on biological samples for a corresponding assay workflow.

In a step 192, the cluster manager 22 can consolidate cluster resources into a multi-instrument assay workflow—based on the instrument resource descriptions 110.1, 110.2 and 110.$n$ of the plurality of laboratory instruments 10, 10PRE, 10POST, 10AI, 10VI, 10TRANS that will be part of the multi-instrument assay workflow 12. Thereafter, the cluster manager 22 can update its list of processing capabilities, the updated list of processing capabilities further comprising processing capabilities of the multi-instrument assay workflow 12 corresponding to the assay workflow description.

Hence, upon receipt of a test order for processing a biological sample which can require an assay workflow, the laboratory information system 30 can transmit a test order(s) to the corresponding cluster manager 22 comprising the multi-instrument assay workflow 12. Upon receipt 160 of such test order(s), the cluster manager 22 can instruct 175 all laboratory instruments 10, 10PRE, 10POST, 10AI, 10VI, 10TRANS of the multi-instrument assay workflow 12 to carry out the respective assay workflow on the biological sample.

The laboratory instruments 10, 10PRE, 10POST, 10AI, 10VI, 10TRANS of the multi-instrument assay workflow 12 can then carry out processing of the biological sample 180.1, 180.2 and 180.3 as instructed by the cluster manager 22.

As shown with dashed lines on FIG. 4, according to further embodiments, in a step 194, the cluster manager 22 can set up peer-to-peer data communication(s) between laboratory instruments 10, 10PRE, 10POST, 10AI, 10VI, 10TRANS of a multi-instrument assay workflow 12. Laboratory instruments 10, 10PRE, 10POST, 10AI, 10VI, 10TRANS of the multi-instrument assay workflow 12 can then exchange analytical data directly via the first peer-to-peer data communication. Alternatively, or additionally, the cluster manager 22 can set up a brokered data communication between laboratory instruments 10, 10PRE, 10POST, 10AI, 10VI, 10TRANS of the multi-instrument assay workflow 12 via a communication broker 19, wherein the respective laboratory instruments 10, 10PRE, 10POST, 10AI, 10VI, 10TRANS of the multi-instrument assay workflow 12 can then exchange analytical data via the communication broker 19. The specifics of peer-to-peer data communication and brokered data communication will be discussed in greater detail with reference to FIG. 9.

FIGS. 5-10 show block diagrams of various embodiments of the disclosed laboratory system 1 configured to carry out one of the methods according to embodiments of the above method.

Figure 5:
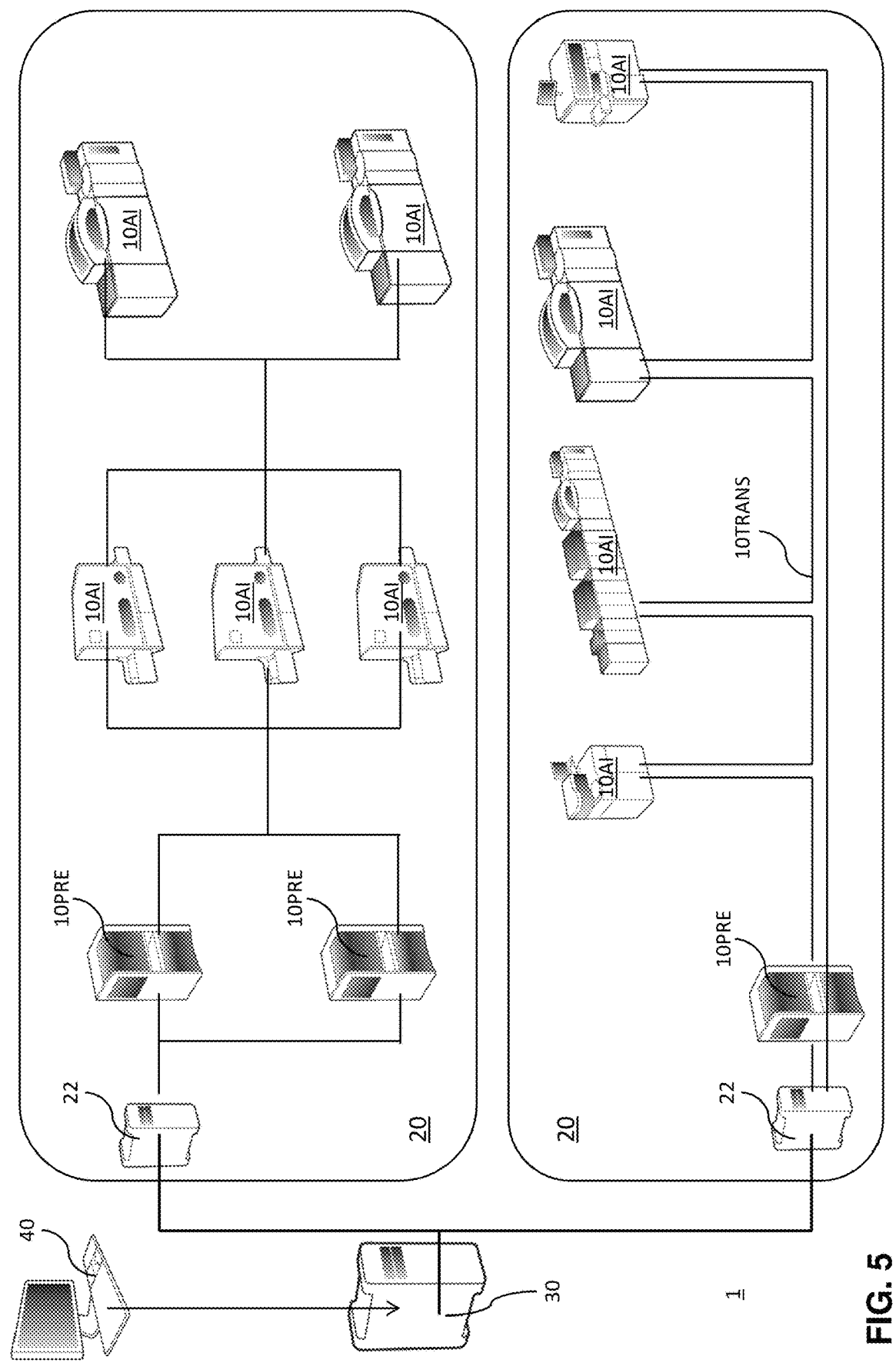
FIG. 5 illustrates a highly schematic block diagram illustrating load balancing between multiple instruments within instrument clusters according to an embodiment of the present disclosure.

FIG. 5 shows a highly schematic block diagram of an embodiment of the disclosed laboratory system 1 comprising several instrument clusters 20. The figure shows two different kinds of instrument clusters 20, one (upper cluster) is laid out in particular for a sequential processing of a biological sample. As it can be seen, this instrument cluster 20 can comprise two pre-analytical laboratory instruments 10PRE, three analytical instruments 10AI of a first type and two analytical instruments 10AI of a second type, all in sequence. Furthermore, the upper instrument cluster 20 of FIG. 5 is provided with several instruments 10PRE, 10AI of the same type to increase throughput by parallel processing of different samples. These instruments 10PRE, 10AI, 10VI can be configured such that the cluster manager 22 may perform load-balancing between instruments with identical/equivalent resources, both for increasing throughput of the instrument cluster 20, but also to increase availability by providing redundancy. In this way, if one of the instruments 10PRE, 10AI, 10VI fails, another one with identical/equivalent resources can take over.

According to further embodiments of the disclosed laboratory system 1, one or more of the instrument clusters 20 can comprise a transportation system 10TRANS for transporting biological samples and/or consumables between the plurality of laboratory instruments 10, 10PRE, 10POST, 10AI, 10VI. One example of such an embodiment is illustrated in FIG. 5. According to an even further embodiment of the disclosed laboratory system 1, one or more of the instrument clusters 20 can comprise a first and second of transportation systems forming a transportation instrument cluster 20, the first and second transportation systems being linked to each other for transporting biological samples and/or consumables between a first and second laboratory instruments 10, 10PRE, 10POST, 10AI, 10VI, wherein the first laboratory instrument 10, 10PRE, 10POST, 10AI, 10VI can be connected to the first transportation system while the second laboratory instrument 10, 10PRE, 10POST, 10AI, 10VI can be connected to the second transportation system. In other words, the first and second of transportation systems of a transportation instrument cluster 20 are configured to be able to "hand-over" biological samples and/or consumables between each other, thereby extending the "reach" of the transportation instrument cluster 20 beyond the capabilities of a single transportation system 10TRANS.

On the other hand, an instrument cluster 20 (the lower one on FIG. 6) may be laid out in particular for parallel processing of multiple test orders for a certain biological sample. Parallelization can be advantageous in particular for accelerating the processing of a biological sample when multiple analytical tests need to be performed on the same sample. In this case, aliquots of the biological sample can be created by a pre-analytical instrument 10PRE which can then be processed simultaneously by the several analytical instruments 10AI.

It can be noted, that according to the disclosed method/system, such optimizations (to achieve load-balancing, fault-tolerance and parallelization) can be managed on an instrument cluster 20 level by way of resource scheduling and necessary information (such as capabilities and availabilities) being forwarded to the laboratory information system 30, a higher level cluster, thus resource scheduling achieving transparency.

Figure 6:
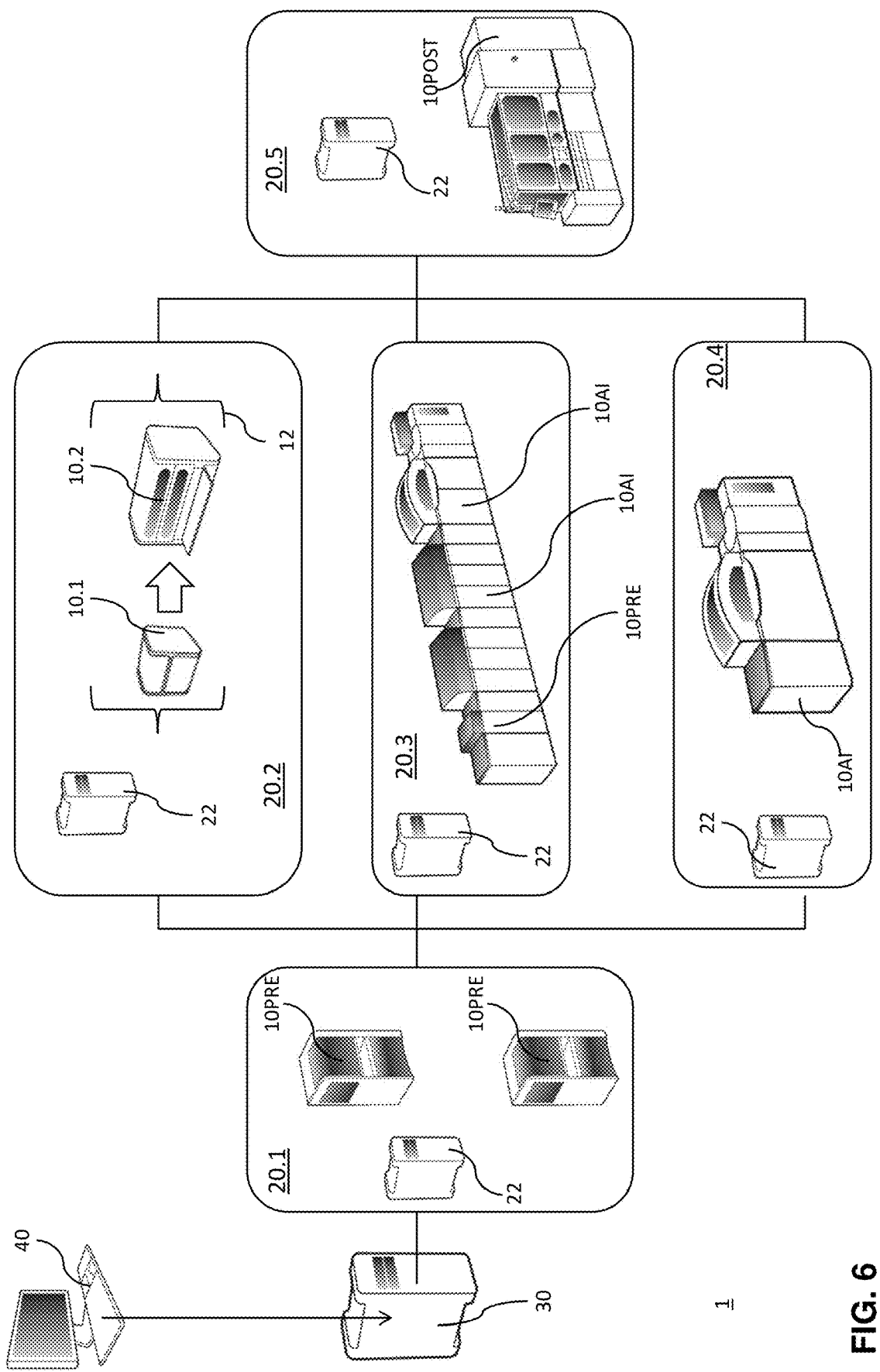
FIG. 6 illustrates a highly schematic block diagram illustrating a multi-instrument assay workflow within an instrument cluster, comprising a first laboratory instrument and a second laboratory instrument according to an embodiment of the present disclosure.

FIG. 6 shows a highly schematic block diagram of an embodiment of the disclosed laboratory system 1 comprising several instrument clusters 20, illustrating a multi-instrument assay workflow 12 within an instrument cluster 20, comprising a first laboratory instrument 10.1 for sample preparation and a second laboratory instrument 10.2 for measurement, while the pre-analytical instrument 10PRE and the post-analytical instrument 10POST may not be part of the workflow. Furthermore, FIG. 6 shows a pre-analytical instrument cluster 20.1 comprising pre-analytical instruments 10PRE, a three analytical clusters 20.2, 20.3 and 20.4 as well as a post-analytical cluster 20.5 comprising a post-analytical instrument 10POST. According to some embodiments, the three analytical clusters 20.2, 20.3 and 20.4 may be each dedicated to a certain work area, such as e.g., analytical cluster 20.2 for nucleic acid testing NAT, analytical cluster 20.3 for serum work area and/or coagulation and analytical cluster 20.4 for hematology.

Figure 7:
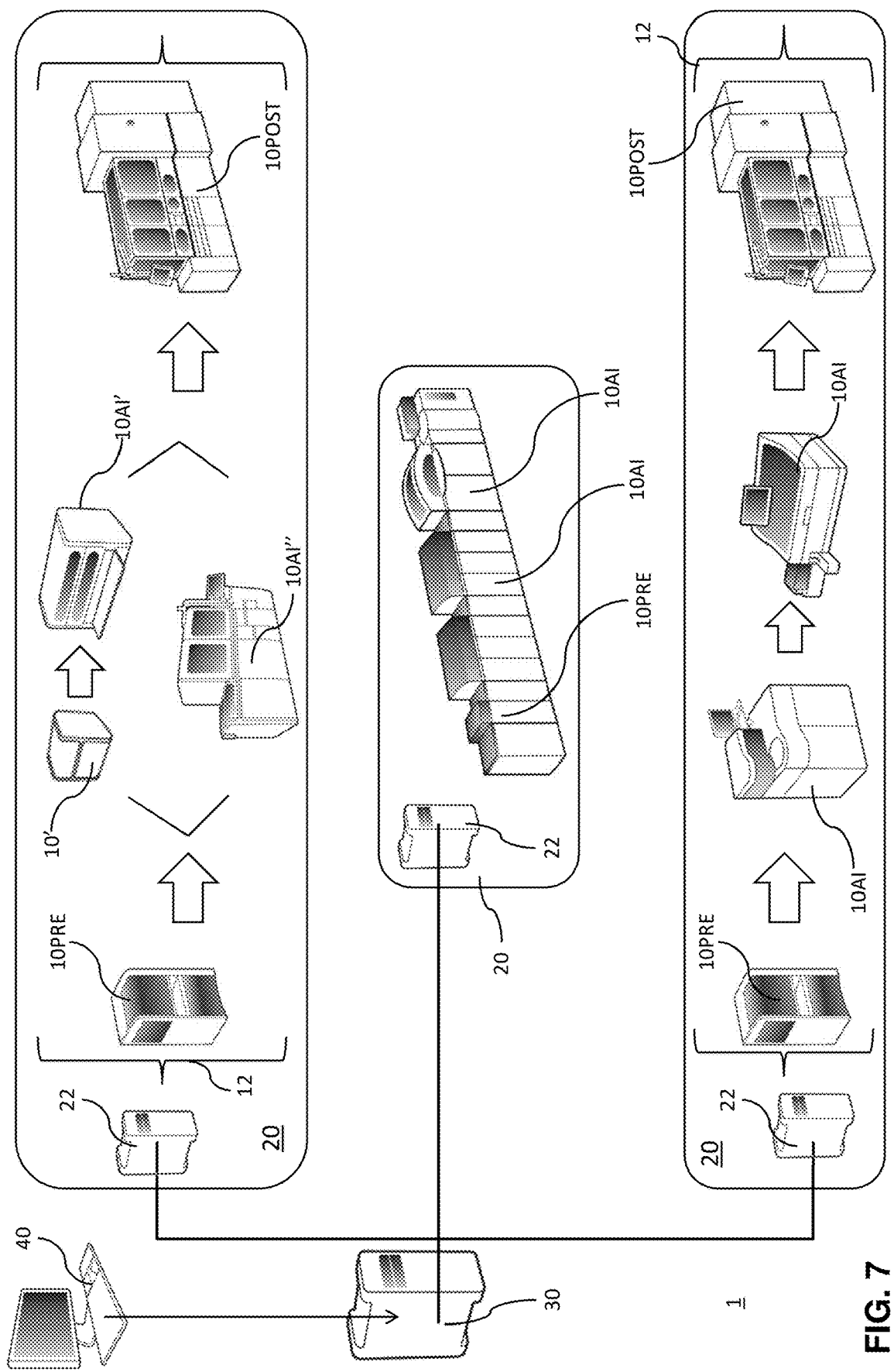
FIG. 7 illustrates a highly schematic block diagram illustrating several multi-instrument assay workflows and illustrating how different multi-instrument assay workflows within an instrument cluster may share instruments according to an embodiment of the present disclosure.

On the other hand, FIG. 7 shows multi-instrument assay workflows 12 comprising pre-analytical instrument 10PRE, analytical instruments 10AI and also the post-analytical instruments 10POST. As illustrated on the uppermost instrument cluster 20, a multi-instrument assay workflow 12 may comprise load-balancing within, wherein for certain loads, a lower throughput series of two instruments 10' and 10AI' can be assigned to process certain types of test orders, while a single higher-throughput integrated instrument 10AI" can be assigned to process a high-volume test order(s).

Figure 8:
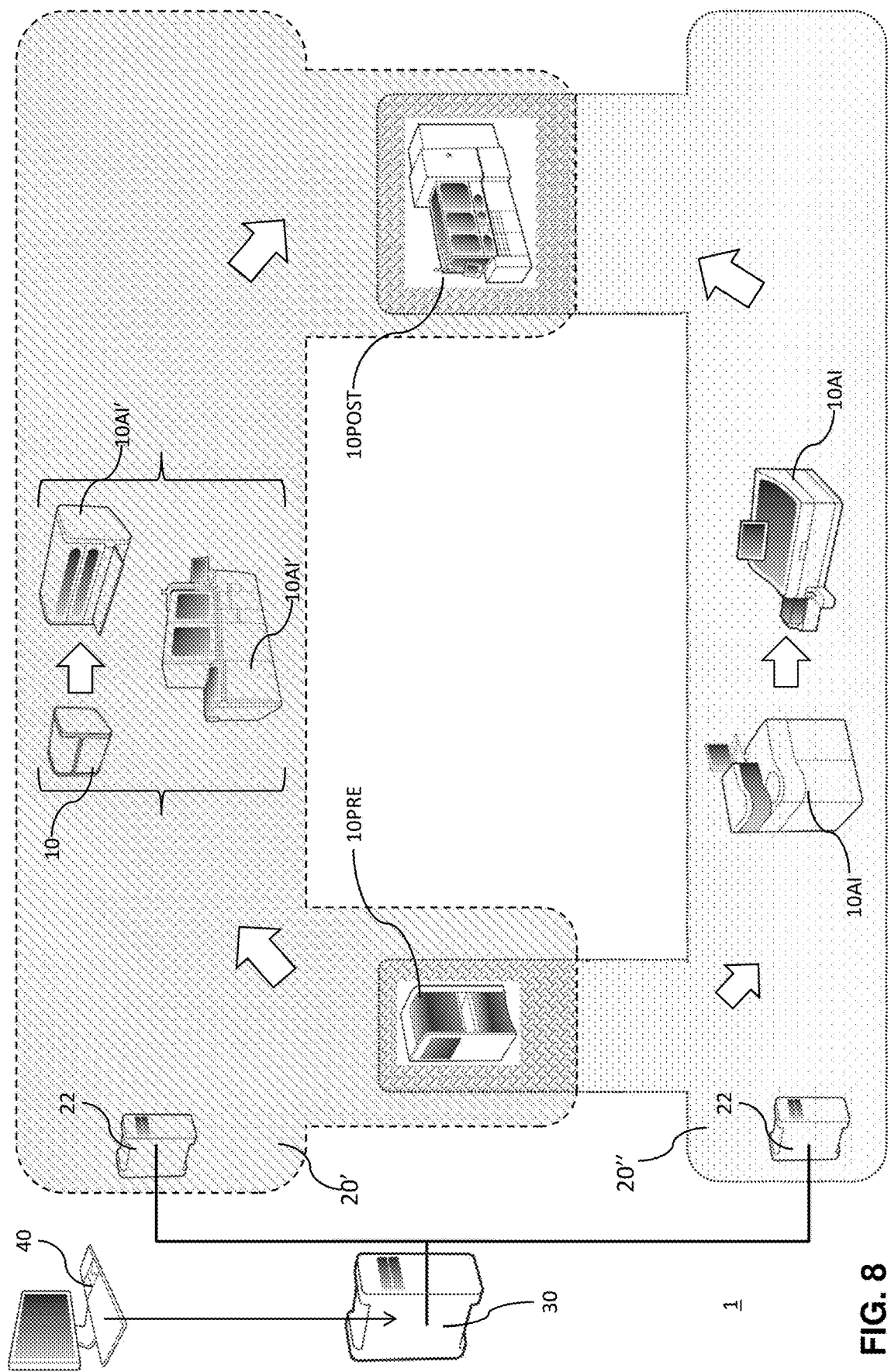
FIG. 8 illustrates a highly schematic block diagram illustrating several instrument clusters sharing instruments between them, e.g. pre- and post-analytic instruments being shared between instrument clusters according to an embodiment of the present disclosure.

As mentioned above briefly, according to some embodiments, the grouping of laboratory instruments into clusters can occur on a logical level. FIG. 8 shows a highly schematic block diagram of such an embodiment of the laboratory system 1, wherein several instrument clusters 20' respectively 20" share instruments 10PRE and 10POST between them. This can be particularly advantageous since often very different analytical tests do require similar or identical pre- and post-analytics. In the example shown on FIG. 8, the first instrument cluster 20' can comprise analytical instruments 10AI' for nucleic acid testing NAT. On the other hand, the second instrument cluster 20" can comprise analytical instruments 10AI' from the serum work area. Nevertheless, as both types of analytical instruments need the same pre- and post-analytical resources, the logical clustering wherein an instrument cluster 20' for nucleic acid testing and a serum work area instrument cluster 20" share the same pre-analytical instrument 10PRE (e.g. a sample tube de-capper and sorter) and post-analytical instrument 10POST (e.g. a sample archiving unit) can provide great flexibility and economy to laboratories.

Figure 9:
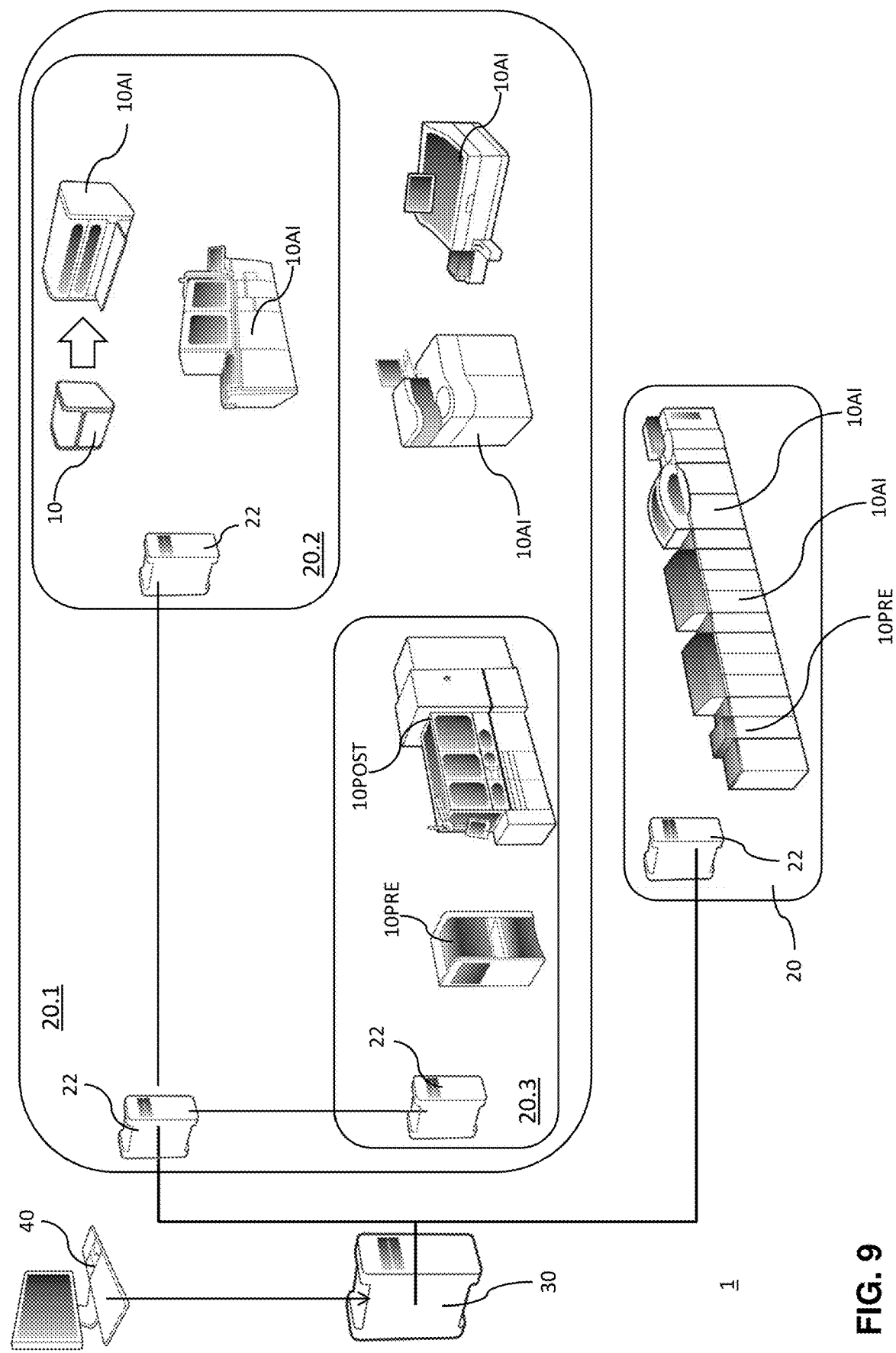
FIG. 9 illustrates a highly schematic block diagram illustrating nested instrument clusters, i.e., a first instrument cluster comprising a second instrument cluster according to an embodiment of the present disclosure.

FIG. 9 shows a further aspect of the method/system disclosed herein, namely the nesting of instrument clusters. In particular, FIG. 9 shows a highly schematic block diagram of an embodiment of the disclosed laboratory system 1 comprising several instrument clusters 20, 20.1 and 20.2, wherein a first instrument cluster 20.1 comprises a second instrument cluster 20.2 and 20.3. Nesting of instrument clusters can be advantageous for example when there is a need to group laboratory instruments both by laboratory discipline (e.g., cluster 20.2 for nucleic acid testing) but also by laboratory location. Furthermore, FIG. 9 shows the clustering of a pre-analytical instrument 10PRE and post-analytical instrument 10POST into a separate cluster 20.3.

Figure 10:
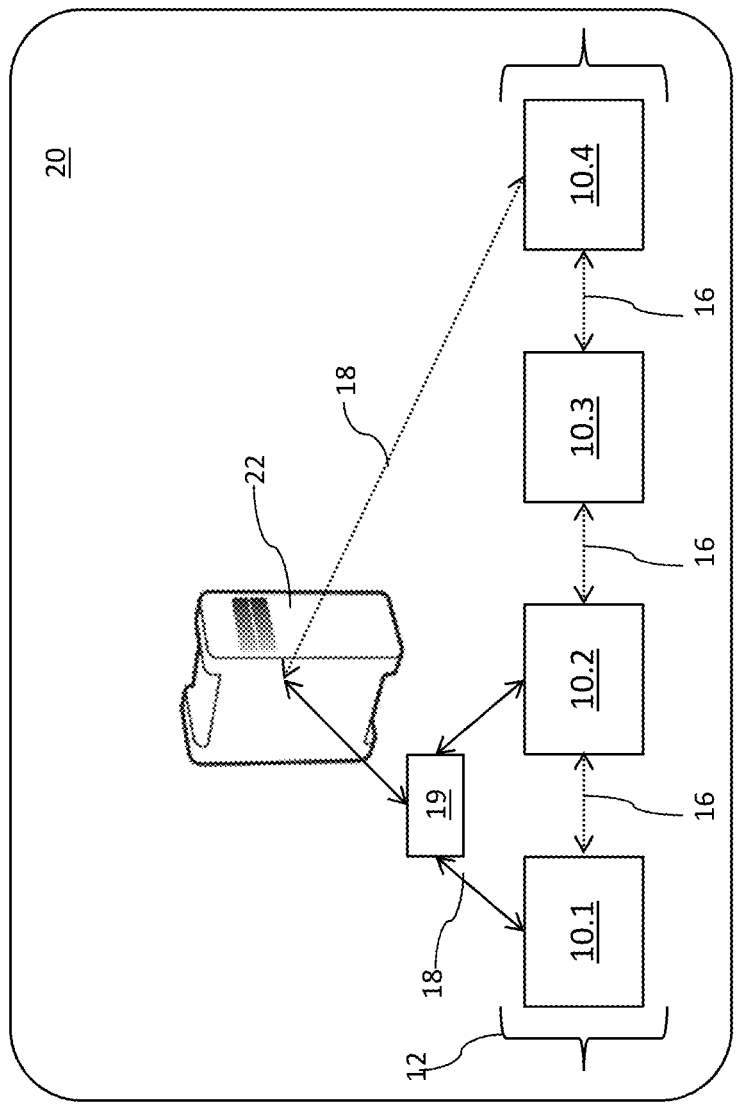
FIG. 10 illustrates a highly schematic block diagram of a single instrument cluster comprising a multi-instrument assay workflow within which the individual instruments are communicatively connected by peer-to-peer data communications as well as further instruments being interconnected by brokered data communications according to an embodiment of the present disclosure.

FIG. 10 shows a highly schematic block diagram of a single instrument cluster 20 according to a further embodiment, comprising a multi-instrument assay workflow 12 within which the individual instruments 10.1 through 10.4 are communicatively connected by peer-to-peer data communications 16. A peer-to-peer data communication 16 between the second laboratory instrument 10.2 and the third laboratory instrument 10.2 of the multi-instrument assay workflow 12 can be advantageous when a high amount of analytical data needs to be exchanged between two instruments 10.2 respectively 10.3.

On the other hand, laboratory instruments 10.1 and 10.2 and the cluster manager 22 can be inter-connected via a brokered data communication 18 via a communication broker 19. According to various embodiments, the communication broker 19 can be a separate entity or can be comprised by one of the plurality of cluster managers 22. Generally, a brokered data communication can be employed when more than two modules (instruments of cluster managers) need to communicate with each other. Furthermore, a brokered data communication 18 can be advantageous, in particular, when process control data (such as resource handling, prioritization, etc.) needs to be exchanged. In this case, a communication broker 19 which has access to all communication can be advantageous. Furthermore, a brokered data communication 18 can be advantageous when measurement results are transmitted by an instrument 10, 10PRE, 10POST, 10AI, 10VI, 10TRANS to the cluster manager 22.

Figure 11:
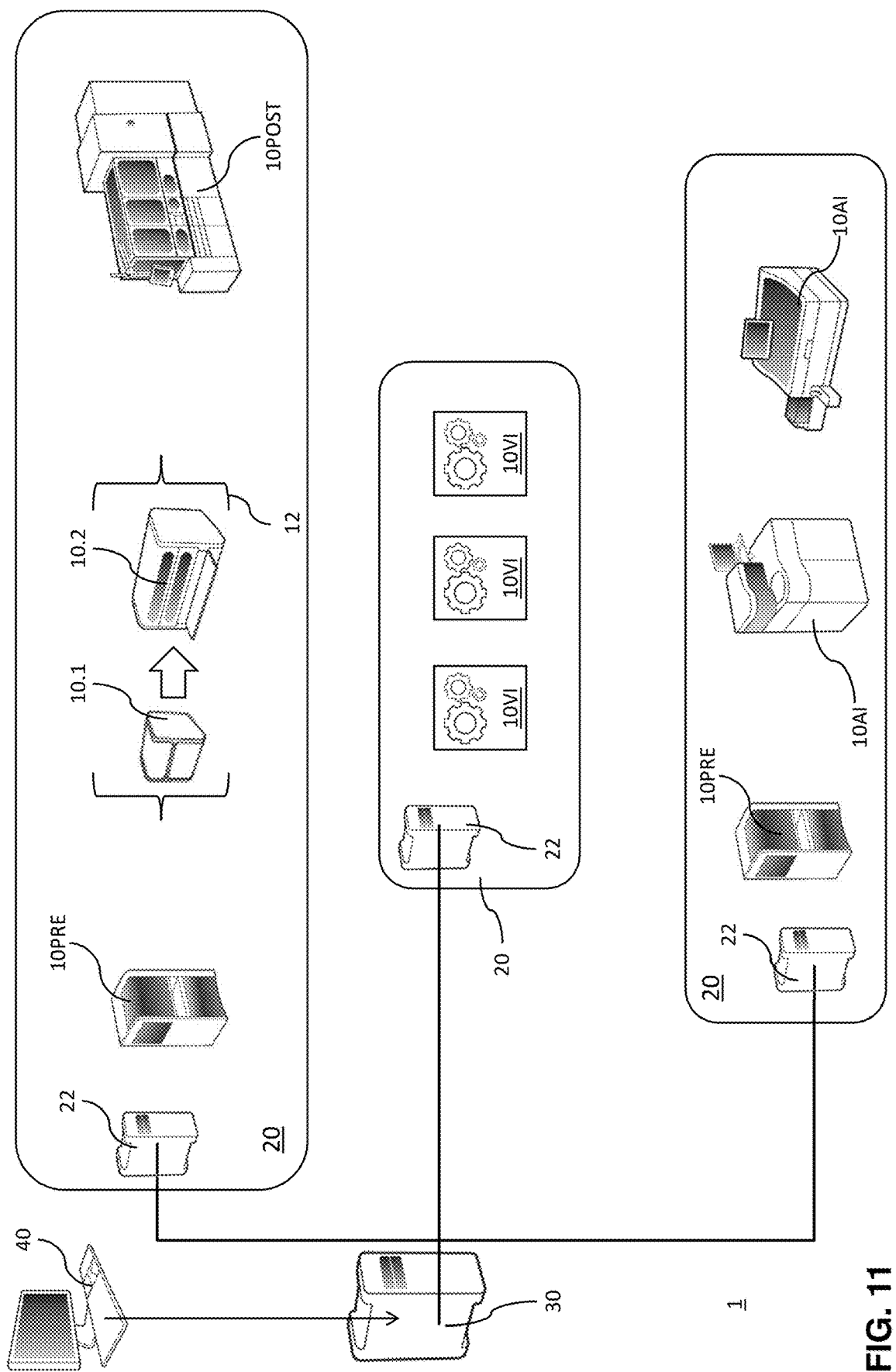
FIG. 11 illustrates a highly schematic block diagram illustrating an instrument cluster comprising a plurality of virtual instruments according to an embodiment of the present disclosure.

FIG. 11 shows a highly schematic block diagram of a further embodiment of the disclosed laboratory system 1, wherein one of the instrument clusters 20 comprises a plurality of virtual instruments 10VI, a virtual instrument 10VI comprising an algorithm calculator configured to apply a clinical algorithm on input data in order to provide interpretation support data based thereon.

According to further embodiments, the cluster manager 22 can comprise a cluster resource manager and a cluster workflow manager. The cluster resource manager can be configured to maintain the inventory of cluster resources and also to publishing a list of processing capabilities of the respective instrument cluster 20 to the laboratory information system 30. The cluster workflow manager can be configured to: receive the test order from the laboratory information system 30; assign resources of the plurality of laboratory instruments 10, 10PRE, 10POST, 10AI, 10VI, 10TRANS of the instrument cluster 20 for the processing step(s) on the respective biological sample corresponding to the test order in view of the inventory of cluster resources; and to instruct one or more laboratory instrument(s) 10, 10PRE, 10POST, 10AI, 10VI, 10TRANS of the instrument cluster 20 to carry out the respective processing step(s) on the biological sample. In other words, the functionality of managing the resources and managing the processing workflow of the samples can be split within each instrument cluster 20, between the cluster resource manager respectively the cluster workflow manager.

Further disclosed and proposed is a computer program product including computer-executable instructions for performing the disclosed method in one or more of the embodiments when the program is executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

Further disclosed and proposed is a computer program product comprising instructions which, when executed by a computer system, cause a laboratory system to perform the method according to one or more of the embodiments disclosed herein.

As used herein, a computer program product can refer to the program as a tradable product. The product may generally exist in any format, such as in a paper format, or on a computer-readable data carrier on premise or located at a remote location. Specifically, the computer program product may be distributed over a data network. Furthermore, not only the computer program product, but also the execution hardware may be located on premise or in a cloud environment.

Further disclosed and proposed is a computer-readable medium comprising instructions which, when executed by a computer system, can cause a laboratory system to perform the method according to one or more of the embodiments disclosed herein.

Further disclosed and proposed is a modulated data signal comprising instructions which, when executed by a computer system, can cause a laboratory system to perform the method according to one or more of the embodiments disclosed herein.

Referring to the computer-implemented aspects of the disclosed method, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer implemented method for operating a laboratory system comprising a plurality of laboratory instruments for processing biological samples and a laboratory information system, wherein each laboratory instrument has processing capabilities configured to execute specific processing steps on the biological samples, the method comprising:

grouping one or more of the plurality of laboratory instruments into one or more instrument cluster(s) and providing a cluster manager for each instrument cluster(s);

within each instrument cluster, publishing the respective instrument resource description of each laboratory instrument(s) for the cluster manager, wherein the instrument resource description comprises a list of hardware and/or software resources of the laboratory instrument;

maintaining an inventory of cluster resources of the instrument cluster by each cluster manager, wherein the inventory of cluster resources comprises a consolidated collection based on the instrument resource descriptions of each of the laboratory instruments of the respective instrument cluster;

publishing a list of processing capabilities of the respective instrument cluster to the laboratory information system by each cluster manager, wherein the list of processing capabilities is indicative of processing steps that the respective instrument cluster is able to carry out based on the inventory of cluster resources, and wherein, for at least one instrument cluster, the list of processing capabilities comprises processing capabilities of a multi-instrument assay workflow, wherein the multi-instrument assay workflow provides specific processing steps to be collaboratively processed by different types of laboratory instruments in the plurality of laboratory instruments;

receiving a biological sample by the laboratory system;

receiving a test order corresponding to the biological sample by the laboratory information system, wherein the test order is indicative of processing step(s) to be carried out on respective biological sample;

assigning processing of the test order on the biological sample to the one or more instrument clusters by the laboratory information system according to the list of processing capabilities of the instrument clusters;

forwarding one or more test order(s) by the laboratory information system to one or more cluster manager(s), wherein at least one of the one or more test order(s) comprises the multi-instrument assay workflow;

receiving the test order(s) from the laboratory information system by the one or more cluster manager(s);

assigning by each cluster manager resources of the plurality of laboratory instruments of the instrument cluster for the processing step(s) on the biological sample corresponding to the test order in view of the inventory of cluster resources;

instructing one or more laboratory instrument(s) of the instrument cluster by each cluster manager to carry out the respective processing step(s) on the biological sample, wherein, for the at least one instrument cluster whose list of processing capabilities comprises processing capabilities of the multi-instrument assay workflow, the cluster manager instructs at least two different types of laboratory instruments in the plurality of laboratory instruments to carry out the multi-instrument assay workflow; and carrying out the respective processing step(s) on the biological sample by each laboratory instrument as instructed by the cluster manager.

2. The computer implemented method according to claim 1, wherein the instrument resource descriptions of the laboratory instruments further comprise an indication of current and/or estimated availability of the hardware and/or software resources and wherein the list of processing capabilities of the respective instrument cluster further comprises an indication of current and/or estimated availability to carry the respective processing steps.

3. The computer implemented method according to claim 1, wherein the instrument resource descriptions of the laboratory instruments further comprise an indication of current and/or estimated capacity of the hardware and/or software resources and wherein the list of processing capabilities of the respective instrument cluster further comprises an indication of current and/or estimated capacity to carry the respective processing steps.

4. The computer implemented method according to claim 3, further comprises, assigning resources of the plurality of laboratory instruments by the cluster manager for the processing step(s) on the respective biological sample in view of the availability and/or capacity of the resources of the laboratory instruments of the respective instrument cluster to provide load balancing between laboratory instruments with the same resources and/or to ensure timely processing of the biological sample.

5. The computer implemented method according to claim 1, further comprises, publishing an update of its instrument resource descriptions by one or more of the plurality of laboratory instruments at regular intervals and/or upon a change of its hardware and/or software resources; and updating the inventory of cluster resources by one or more of the cluster managers based on the update(s) of instrument resource descriptions.

6. The computer implemented method according to claim 4, further comprises, transmitting by the cluster manager an updated list of processing capabilities to the laboratory information system if upon updating the inventory of cluster resources based on the update(s) of instrument resource descriptions, the respective instrument cluster is no longer able to carry out a particular processing step; and transmitting by the cluster manager an updated list of processing capabilities to the laboratory information system such as updating the availability and/or capacity to carry the particular processing step if upon updating the inventory of cluster resources based on the update(s) of instrument resource descriptions, the overall availability and/or capacity of the instrument cluster to carry out a particular processing step is changed.

7. The computer implemented method according to claim 6, further comprises, re-assigning by the laboratory information system the processing of test orders on the biological sample(s) to another instrument clusters in view of the update of the list of processing capabilities of one or more of the instrument clusters.

8. The computer implemented method according claim 1, further comprises, retrieving by one of the cluster managers an assay workflow description, wherein the assay workflow description comprises a list and sequence of processing steps to be carried out on biological samples for a corresponding assay workflow;

consolidating by the cluster manager resources of a first laboratory instrument and a second laboratory instrument of the plurality of laboratory instruments of the instrument cluster for processing step(s) on the biological sample according to the list and sequence of processing steps of the assay workflow description, thereby setting up a multi-instrument assay workflow;

updating by the cluster manager its list of processing capabilities;

forwarding test order(s) by the laboratory information system to the corresponding cluster managers comprising the multi-instrument assay workflow in the presence of a test order indicative of the assay workflow to be carried out on respective biological sample(s); and instructing the first laboratory instrument and the second laboratory instrument of the multi-instrument assay workflow by the cluster manager to carry out the respective assay workflow on the biological sample in the presence of a test order from the laboratory information system being indicative of the assay workflow to be carried out on respective biological sample(s).

9. The computer implemented method according claim 8, further comprises, setting up by the cluster manager a brokered data communication between the first and a second laboratory instrument of the instrument cluster via a communication broker;

transmitting and/or receiving data between the first laboratory instrument and the second laboratory instrument via the brokered data communication;

setting up a peer-to-peer data communication between the second laboratory instrument and a third laboratory instrument of the multi-instrument assay workflow by the cluster manager; and transmitting and/or receiving analytical data by the second laboratory instrument directly to/from the third laboratory instrument via the peer-to-peer data communication.

10. The computer implemented method according claim 9, wherein the brokered data communication uses a publisher-subscriber communication pattern and the peer-to-peer data communication uses a request-response communication pattern.

11. A non-transitory computer-readable medium storing instructions thereon which, when executed by a computer system, cause a laboratory system to perform the steps of the method according to claim 1.

* * * * *